(12) United States Patent
Harris et al.

(10) Patent No.: US 11,246,723 B2
(45) Date of Patent: Feb. 15, 2022

(54) LOWER LIMB PROSTHESIS COMPRISING A HYDRAULIC DAMPING AND A VACUUM GENERATING MECHANISM

(71) Applicant: BLATCHFORD PRODUCTS LIMITED, Basingstoke (GB)

(72) Inventors: Graham Harris, Hatch Warren (GB); Mir Saeed Zahedi, London (GB); Fadi Abimosleh, Springboro, OH (US)

(73) Assignee: BLATCHFORD PRODUCTS LIMITED, Basingstoke (GB)

( * ) Notice: Subject to any disclaimer, the term of this patent is extended or adjusted under 35 U.S.C. 154(b) by 177 days.

(21) Appl. No.: 16/535,822

(22) Filed: Aug. 8, 2019

(65) Prior Publication Data
US 2020/0069440 A1 Mar. 5, 2020

Related U.S. Application Data

(63) Continuation of application No. 15/556,130, filed as application No. PCT/GB2016/050609 on Mar. 7, 2016, now Pat. No. 10,406,001.

(30) Foreign Application Priority Data

Mar. 6, 2015 (GB) ..................... 1503814

(51) Int. Cl.
*A61F 2/66* (2006.01)
*A61F 2/74* (2006.01)
(Continued)

(52) U.S. Cl.
CPC .......... *A61F 2/7812* (2013.01); *A61F 2/6607* (2013.01); *A61F 2/80* (2013.01); *A61F 2/74* (2021.08); *A61F 2/742* (2021.08); *A61F 2/748* (2021.08); *A61F 2002/5001* (2013.01); *A61F 2002/5003* (2013.01); *A61F 2002/5006* (2013.01); *A61F 2002/5073* (2013.01); *A61F 2002/607* (2013.01);
(Continued)

(58) Field of Classification Search
CPC .......... A61F 2002/742; A61F 2002/747; A61F 2/741; A61F 2/748
See application file for complete search history.

(56) References Cited

U.S. PATENT DOCUMENTS

| 8,308,815 | B2 | 11/2012 | McCarthy |
|---|---|---|---|
| 2001/0016781 | A1 | 8/2001 | Caspers |

(Continued)

FOREIGN PATENT DOCUMENTS

| GB | 2338653 A | 12/1999 |
|---|---|---|
| WO | 9908621 A1 | 2/1999 |

(Continued)

*Primary Examiner* — David H Willse
(74) *Attorney, Agent, or Firm* — Volpe Koenig

(57) ABSTRACT

A lower limb prosthesis comprises a foot component and an ankle unit pivotally mounted to the foot component. The ankle unit comprises an ankle joint mechanism comprising a hydraulic piston and cylinder assembly for providing hydraulic damping whenever the ankle joint flexes, and a vacuum mechanism comprising a pneumatic piston and cylinder assembly for generating a vacuum. The hydraulic and pneumatic piston and cylinder assemblies are arranged such that the vacuum mechanism generates a vacuum during plantar-flexion of the ankle unit.

21 Claims, 11 Drawing Sheets

(51) Int. Cl.
*A61F 2/80* (2006.01)
*A61F 2/78* (2006.01)
A61F 2/50 (2006.01)
A61F 2/60 (2006.01)

(52) U.S. Cl.
CPC .............. *A61F 2002/6657* (2013.01); *A61F 2002/7818* (2013.01); *A61F 2002/802* (2013.01); *A61F 2002/805* (2013.01); *A61F 2002/807* (2013.01)

(56) References Cited

U.S. PATENT DOCUMENTS

| | | |
|---|---|---|
| 2003/0191539 A1* | 10/2003 | Caspers .................... A61F 2/80 623/35 |
| 2005/0143838 A1 | 6/2005 | Collier |
| 2007/0055383 A1 | 3/2007 | King |
| 2010/0312360 A1 | 12/2010 | Caspers |
| 2013/0211544 A1 | 8/2013 | Jonsson et al. |
| 2014/0371874 A1 | 12/2014 | Wu et al. |
| 2016/0058583 A1 | 3/2016 | Hines |

FOREIGN PATENT DOCUMENTS

| | | |
|---|---|---|
| WO | 2008071975 A1 | 6/2008 |
| WO | 2008103917 A1 | 8/2008 |
| WO | 2009015896 A1 | 2/2009 |
| WO | 2014109720 A1 | 7/2014 |
| WO | 2016032609 A1 | 3/2016 |

* cited by examiner

LOWER LIMB PROSTHESIS COMPRISING A HYDRAULIC DAMPING AND A VACUUM GENERATING MECHANISM

CROSS REFERENCE TO RELATED APPLICATION

This application is a continuation of U.S. application Ser. No. 15/556,130, filed Sep. 6, 2017, which issued as U.S. Pat. No. 10,406,001 on Sep. 10, 2019, which is a 371 National Phase filing of PCT/GB2016/050609 with an International Filing Date of Mar. 7, 2016, which claims priority to Great Britain Patent Application No. 1503814.4, filed Mar. 6, 2015, which are incorporated herein by reference as if fully set forth.

FIELD OF INVENTION

The present invention relates to a lower limb prosthesis. In particular, the present invention relates to a lower limb prosthesis for producing a vacuum in a socket for use with a suspension liner.

BACKGROUND

Lower limb prostheses are generally attached to a residual limb by means of a liner and socket arrangement. The lower limb prosthesis is connected to a hollow socket, the shape of which corresponds to the external shape of the residual limb. A liner is placed over the residual limb and the residual limb together with the liner is inserted into the socket.

The residual limb is generally composed of bone, muscles, soft tissue and skin. During ambulation, the soft tissue experiences shear and compression forces at the interface with the liner and socket. The direction of the shear forces changes depending on whether the amputee is applying load to the prosthesis during stance phase or if the weight of the prosthesis is applying a load to the residual limb during swing phase. The alternating nature of these forces can lead to "pistoning" at the stump/socket interface. This effect is exaggerated if the socket is a poor fit or if the limb is heavy, which may be the case with some modern, highly functional prostheses. Whilst a liner made of resilient material moves with the residual limb to cushion and dampen these forces, over time, especially if left unchecked, these shear and compression forces combined with the movement of the residual limb inside the socket can cause discomfort and damage the skin and underlying tissues.

The force applied by the residual limb to the prosthesis can be harvested to expel air from any cavities which may exist between the residual limb and the socket if correct pathways are created to generate a vacuum. Such an arrangement is described in U.S. Pat. No. 8,308,815 B2 to the present applicant, the content of which is incorporated herein by reference, which describes a vacuum-assisted liner system for a socket of a limb prosthesis, for securing the prosthesis to a residual body portion. A vacuum is created directly between the residual body portion and the socket to hold them together and minimise relative movement between them. The system includes a flexible liner made of an impermeable material, at least a distal part of the liner being porous to allow the transport of air and fluid directly away from the residual body portion to the outer surface of the liner. A fabric distribution layer is located over the liner and between the liner and the socket to allow transmission of such extracted air and fluid laterally over the liner to an evacuation port in the socket. Also disclosed is a limb apparatus suspension device incorporating the liner system, and a vacuum suspension device which secures a component such as a stump socket to a residual body portion by creating an evacuated space sealed by intimate contact directly between the socket and a boundary region of the liner.

A snug fit is required between the residual limb, the liner and the socket in order to adequately suspend the lower limb prosthesis from the residual limb, minimise friction associated with the movement of the residual limb inside the socket and to equalise contact pressures. As well as evenly distributing forces on the residual limb when weight is applied to the prosthesis via the socket whilst the lower limb is in contact with ground, the snug fit also contributes to the formation of a vacuum between the liner and the socket so that the lower limb prosthesis remains suspended from the residual limb during the swing phase of the gait cycle. The application of a low pressure to the amputee's residual limb can also aid in sweat management and improve circulation, both of which can have long term health benefits for the amputee. Hence, the presence of a low pressure between the socket and residual limb/liner is a desirable feature of such prostheses and it is an aim of the present invention to harvest the forces and "pistoning" action at the residual limb and provide a lower limb prosthesis incorporating a vacuum source as part of a system for providing a reduced pressure in the socket around the residual lower limb.

US-A1-2005/0143838 to Collier describes a prosthetic device for attachment to a residual limb that includes a pump that is adapted to draw a negative pressure within a socket forming member.

US-A1-2001/0016781 to Caspers describes an osmotic membrane and vacuum system for an artificial limb.

WO-A1-2014/109720 to Duger describes a foot with a vacuum unit activated by ankle motion.

SUMMARY

According to a first aspect of the invention, there is provided a lower limb prosthesis comprising: a foot component; and an ankle unit pivotally mounted to the foot component, the ankle unit comprising: an ankle joint mechanism, the ankle joint mechanism comprising a hydraulic piston and cylinder assembly for providing hydraulic damping whenever the ankle joint flexes, and a vacuum mechanism comprising a pneumatic piston and cylinder assembly for generating a vacuum, wherein the hydraulic and pneumatic piston and cylinder assemblies are arranged such that the vacuum mechanism generates a vacuum during plantar-flexion of the ankle unit.

Since the vacuum mechanism generates a vacuum during plantar-flexion, this allows the vacuum mechanism to draw fluid from a socket which is connected to the vacuum mechanism simultaneously with the expulsion of air from the socket due to transfer of the amputee's weight into the socket.

According to a second aspect of the invention there is provided a lower limb prosthesis comprising: a foot component; and an ankle unit pivotally mounted to the foot component, the ankle unit comprising a body within which is housed: an ankle joint mechanism, the ankle joint mechanism comprising a hydraulic piston and cylinder assembly for providing hydraulic damping whenever the ankle joint flexes; and a vacuum mechanism comprising a pneumatic piston and cylinder assembly for generating a vacuum.

The hydraulic piston and cylinder assembly may comprise a hydraulic piston and a hydraulic cylinder and the pneumatic piston and cylinder assembly may comprise a pneumatic piston and a pneumatic cylinder and the hydraulic and pneumatic pistons may be coaxially mounted.

The hydraulic and pneumatic pistons may be mounted on a common shaft.

The hydraulic and pneumatic cylinders may share a common wall.

The pneumatic cylinder may comprise a pair of pneumatic chambers on each side of the pneumatic piston and the vacuum may be generated in one of the pneumatic chambers when the pneumatic piston moves to expand that chamber, wherein a volume of the pneumatic chamber which generates the vacuum is at a minimum when ankle joint is fully dorsi-flexed.

The ankle joint mechanism may be constructed and arranged such that the hydraulic damping is a predominant resistance to flexion whenever the ankle joint flexes.

One or both of the hydraulic and pneumatic piston and cylinder assemblies may be linear.

The hydraulic cylinder may comprise a pair of hydraulic chambers on each side of the hydraulic piston and the ankle joint mechanism may further comprise a valve arrangement controlling a flow of hydraulic fluid between the chambers of the hydraulic piston and cylinder assembly, the valve arrangement may allow individual setting of dorsi- and plantar-flexion damping resistances.

The valve arrangement may comprise first and second adjustable valves for independently controlling dorsi-flexion damping and plantar-flexion damping respectively.

The ankle joint mechanism may include flexion limiting means limiting dorsi-flexion of the joint mechanism to a dorsi-flexion limit.

The dorsi-flexion limit may be defined by a mechanical end-stop operative by the abutment of one part of the hydraulic cylinder and piston assembly against a second part thereof.

As well as the dorsi-flexion stop allowing energy to be transferred into the toe spring at the end of the dorsi-flexion phase, which assists with toe off during the gait cycle, reaching the dorsi-flexion limit for the hydraulic joint mechanism corresponds with the pneumatic piston of the vacuum mechanism approaching an end wall of the pneumatic cylinder, when the volume of the pneumatic chamber which draws air into the pneumatic cylinder has its minimum volume. This means that at toe off the lower pneumatic chamber has a minimum, near-zero volume, such that it is primed to produce a maximum vacuum once plantar-flexion begins to take place at heel strike.

The end stop may be defined by the hydraulic piston and an end wall of the hydraulic cylinder.

The prosthesis may be arranged such that the ankle joint mechanism reaching its dorsi-flexion limit coincides with the volume of the pneumatic chamber being at its minimum.

The ankle joint mechanism may include two passages in communication with the variable-volume chamber of the hydraulic piston and cylinder assembly, each passage containing a respective non-return valve, one oriented to prevent the flow of fluid from the chamber through its respective passage and the other oriented to prevent the admission of fluid to the chamber through the other passage.

The lower limb prosthesis may include an adjustable damping orifice in at least one of the two passages.

The lower limb prosthesis may include a first adjustable damping orifice that forms part of the passage in communication with the chamber and through which fluid flows during flexion of the joint mechanism in the dorsi-flexion direction.

The lower limb prosthesis may include a second adjustable damping orifice through which fluid flows during flexion of the joint mechanism in the plantar-flexion direction.

The lower limb prosthesis may include a cushioning device for increasing the resistance to dorsi-flexion as flexion of the joint mechanism approaches the dorsi-flexion limit.

The foot component may be an energy-storing foot which is resiliently deformable to allow dorsi-flexion of at least an anterior portion of the foot relative to an ankle-mounting portion of the foot.

The lower limb prosthesis may further comprise: a shin component mounted at its first end to the ankle unit and defining a shin axis; a socket, mounted to a second end of the shin component, the socket comprising an evacuation port; and means for providing the generated vacuum to the evacuation port.

The means for providing the generated vacuum to the evacuation socket may comprise: an inlet port forming part of the ankle unit and which is in communication with the pneumatic cylinder; and a plurality of tubes connected in series with a one-way valve and the inlet port.

The hydraulic and pneumatic piston and cylinder assemblies may share a central axis which is oriented such that said axis is substantially aligned with or parallel to the shin axis.

The ankle joint mechanism may define a medial-lateral joint flexion axis, and the joint flexion axis may be to the anterior of the central axis of the pneumatic and hydraulic piston and cylinder assemblies.

At least one of the foot component and the shin component may include a resilient section allowing resilient dorsi-flexion of at least an anterior portion of the foot component relative to the shin axis.

According to a further aspect of the invention there is provided a system for suspending a lower limb prosthesis from a residuum, the system comprising: a lower limb prosthesis as described above; and a porous suspension liner.

The liner may include a fabric distribution layer disposed over its outer surface. The liner may be perforated at least in a region of the evacuation port.

BRIEF DESCRIPTION OF THE DRAWINGS

The present invention will now be described by way of example only, and with reference to the accompanying drawings in which.

DETAILED DESCRIPTION OF THE PREFERRED EMBODIMENTS

Figure 1:
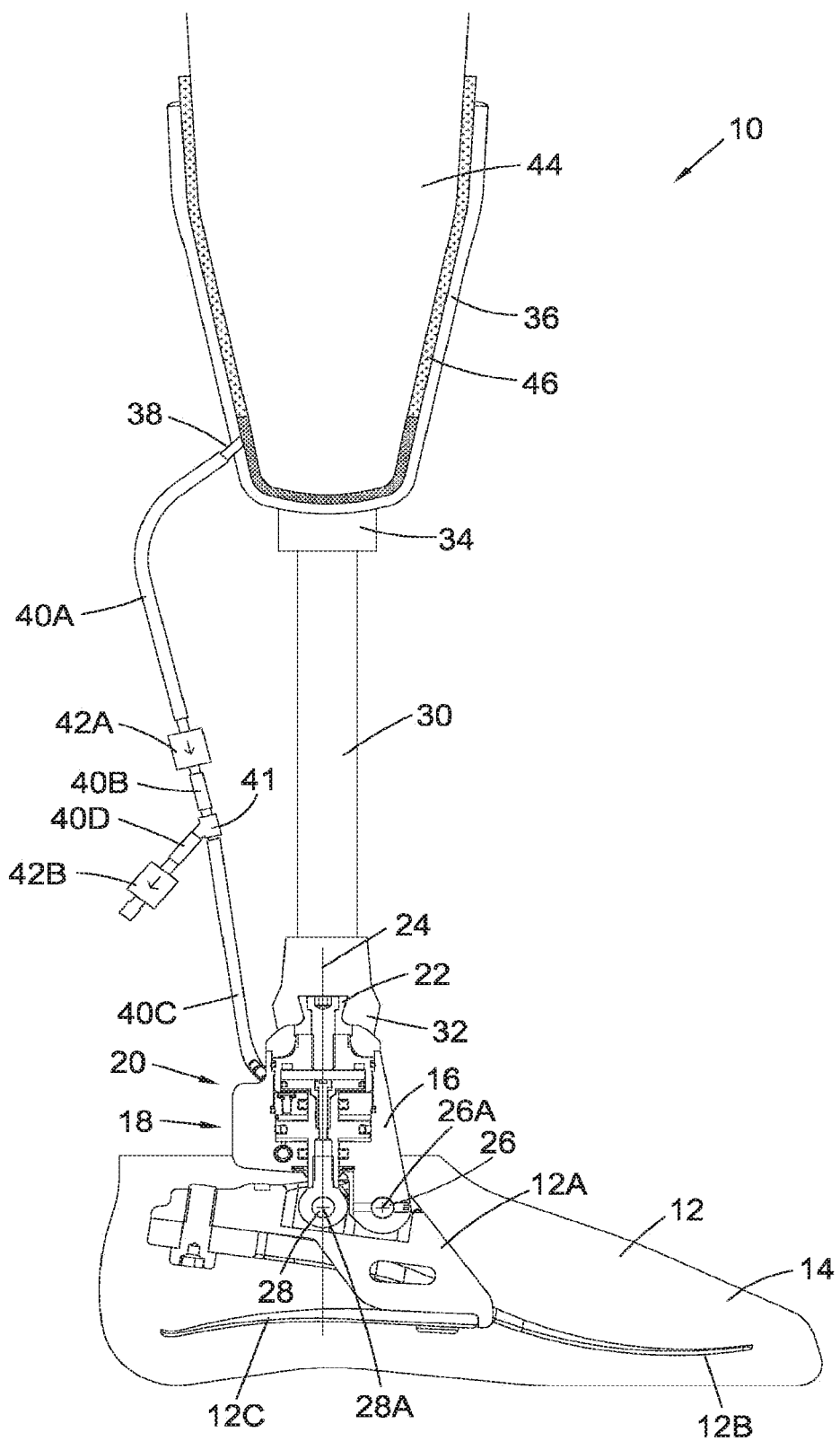
FIG. 1 is a cross-section of a lower limb prosthesis in accordance with an embodiment of the invention, including an ankle unit in accordance with an embodiment of the invention, sectioned on a central anterior-posterior (AP) plane.

Referring to FIG. 1, a lower limb prosthesis 10 in accordance with the invention has a foot component 12 comprising a rigid carrier 12A, a toe spring 12B and a heel spring 12C, the two springs 12B, 12C being independently coupled to the carrier 12A. The foot component 12 is made from a carbon fibre composite material and is surrounded by a foam cosmetic covering 14.

Mounted to the foot component 12 is an ankle unit 16 comprising a joint mechanism 18, a vacuum mechanism 20 and a shin connection interface 22. The shin connection interface 22 defines a shin connection axis 24. The mounting of the ankle unit 16 to the foot component 12 is by way of an ankle flexion pivot 26 and a piston pivot 28. The ankle flexion pivot 26 defines a first ankle flexion axis 26A running in a medial-lateral direction to the anterior of the shin connection axis 24. The piston pivot 28 defines a piston pivot axis 28A running in a medial-lateral direction to the posterior of the first ankle flexion axis 26A.

The ankle unit 16 is connected via the shin connection interface 22 to a shin component 30 at a distal end 32 thereof. A proximal end 34 of the shin component 30 is connected to a socket 36. The socket 36 includes an evacuation port 38 which is connected by means of tubes 40A, 40B, 40C, a first one-way valve 42A and a T-joint 41 to the ankle unit 16. The T-joint 41 is between the tubes 40B and 40C and is connected via a tube 40D to a second one-way valve 42B to allow fluids to exit the tubes 40C, 40D during dorsi-flexion, as is described below. The socket 36 is adapted to receive a residuum 44 on which is donned a porous suspension liner 46. As well as the liner 46 being perforated, the liner 46 may have a fabric distribution layer (not shown) disposed over an external surface of the liner 46 to allow air and fluid flow over the external surface of the liner 46 when it is disposed in the socket 36.

Figure 2:
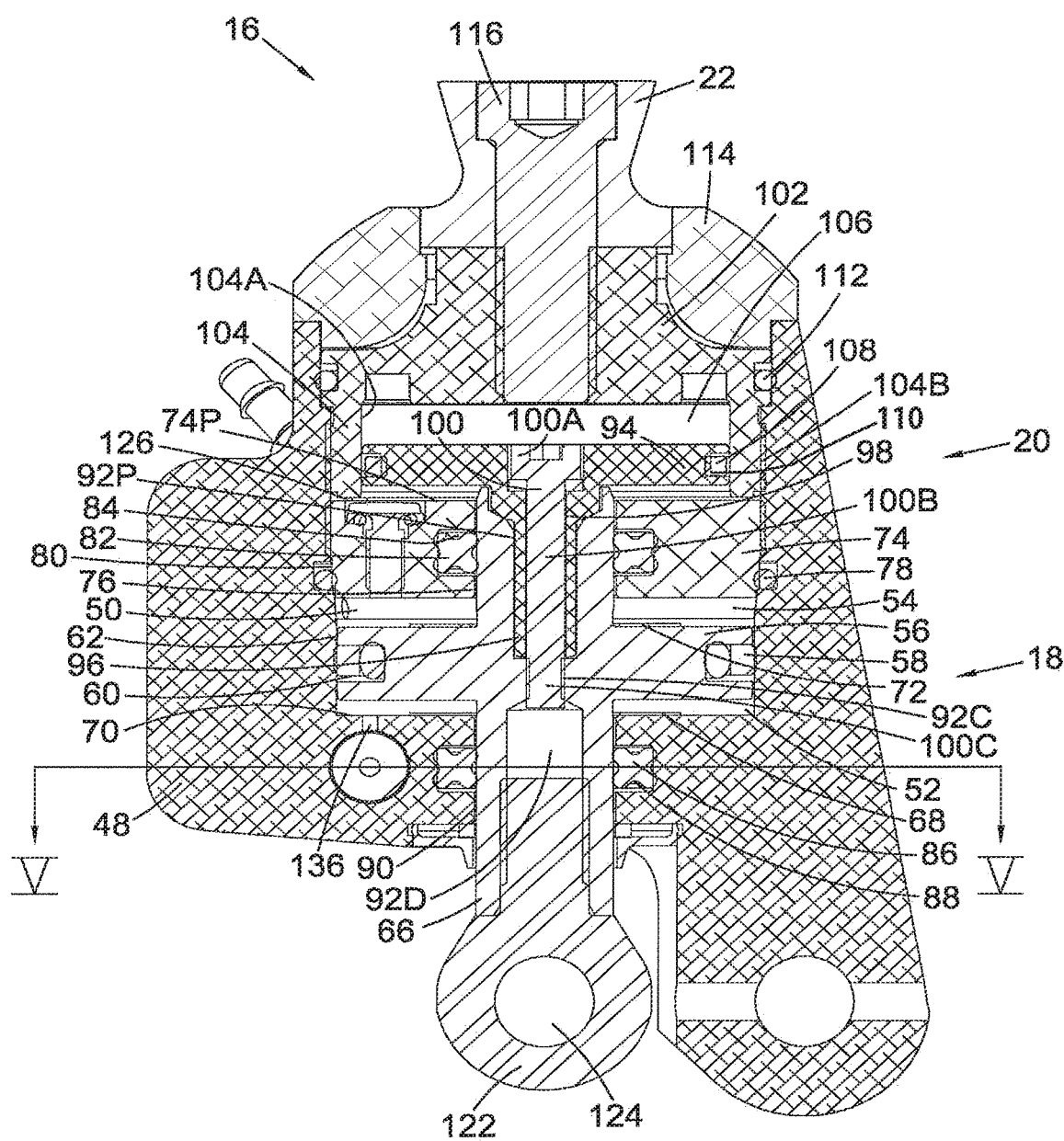
FIG. 2 is a cross-section view, along an anterior-posterior plane, of the ankle unit of FIG. 1 in a neutral position.
Figure 3:
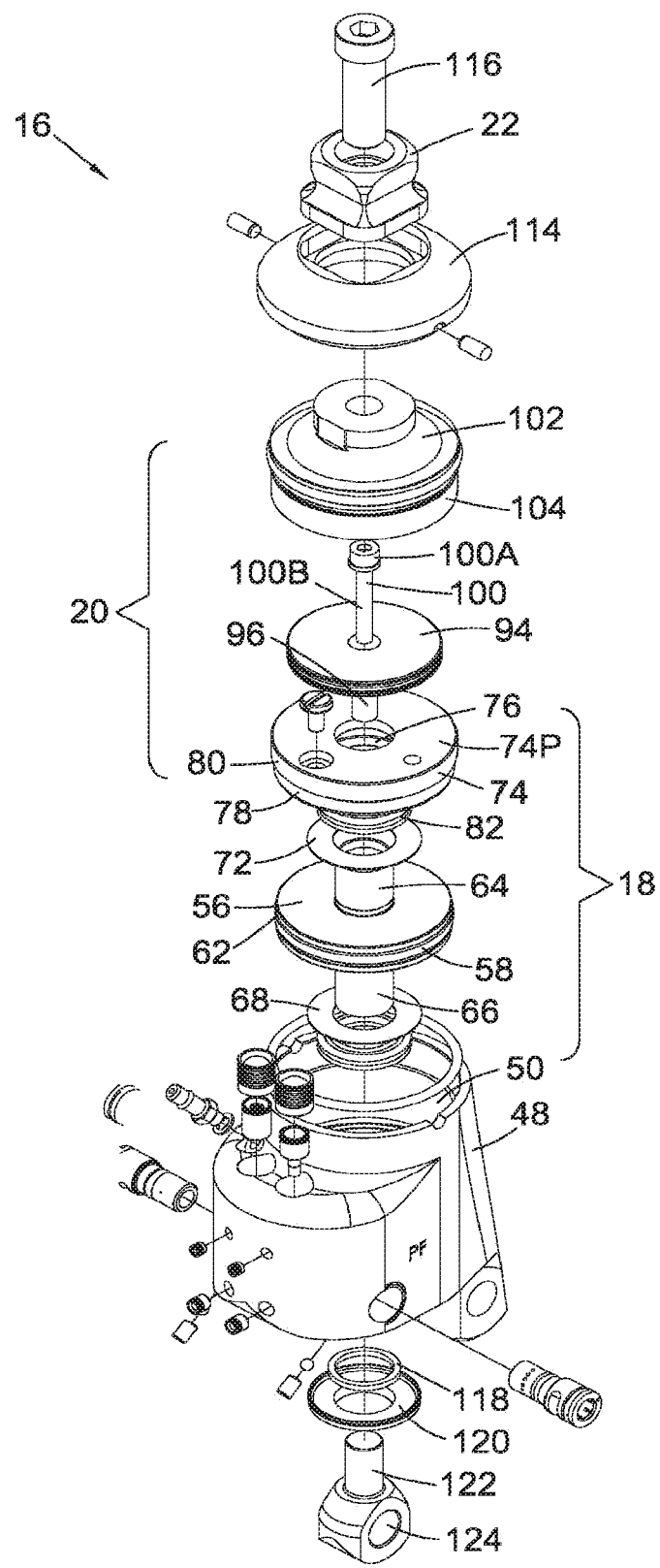
FIG. 3 is a perspective exploded view of the ankle unit of FIG. 2.

The ankle unit 16 is shown in greater detail in FIGS. 2 and 3. A body/housing 48 of the ankle unit 16 houses the ankle joint hydraulic mechanism 18 and the vacuum mechanism 20. An inner surface 50 of the body 48 forms part of a hydraulic cylinder wall 52 of the joint mechanism 18. The cylinder wall 52 defines a hydraulic chamber/cylinder 54 of the joint mechanism 18, within which a joint mechanism hydraulic piston 56 is housed. A glide ring piston seal 58 is disposed in an annular groove 60 around a perimeter 62 of the hydraulic piston 56 for forming a seal between the hydraulic piston 56 and the hydraulic cylinder wall 52. Proximal 64 and distal 66 piston rods extend from the hydraulic piston 56.

A distal nylon washer 68 is disposed around the distal piston rod 66, as a spacer between the hydraulic piston 56 and a distal end wall 70 of the hydraulic cylinder 54. A proximal nylon washer 72 is disposed around the proximal piston rod 64, as a spacer between the hydraulic piston 56 and an end cap 74 of the hydraulic chamber 54. The end cap 74 of the hydraulic chamber 54 is annular, having an end cap bore 76. An O-ring 78 is disposed around a perimeter 80 of the end cap 74, to form a seal between the perimeter 80 and the inner surface 50 of the body 48.

A proximal quad ring 82 is disposed in an internal annular groove 84 in the end cap bore 76. The proximal quad ring 82 forms a seal between the end cap 74 and the proximal piston rod 64. Similarly, a distal quad ring 86 is disposed in an internal annular groove 88 in a distal bore 90 of the housing 48. The distal quad ring 86 forms a seal between the distal piston rod 66 and the housing 48.

A piston bore 92 runs through the proximal piston rod 64, the joint mechanism hydraulic piston 56 and the distal piston rod 66. The piston bore 92 has three portions along its length, namely a proximal bore portion 92P, a central bore portion 92C and a distal bore portion 92D. Parts of the central bore portion 92C and the distal bore portion 92D are threaded. The hydraulic piston 56, hydraulic cylinder 54, the piston rods 64, 66 and associated seals together form a hydraulic piston and cylinder assembly.

A pneumatic piston 94 is connected to the hydraulic piston 56 in the following manner. A tubular shaft 96 extends from the pneumatic piston 94. An outer diameter of the tubular shaft 96 corresponds to an inner diameter of the proximal bore portion 92P of the proximal piston rod 64. A pneumatic piston bore 98 runs through the pneumatic piston 94 and the tubular shaft 96. A pneumatic piston screw 100 has a socket head 100A and a shaft 100B, an end portion 100C of which is threaded. The pneumatic piston screw 100 has a length greater than a length of the pneumatic piston bore 98. The pneumatic piston screw 100 is inserted through the pneumatic piston bore 98. The threaded end portion 100C of the pneumatic piston screw 100 projects from the pneumatic piston bore 98 and is screwed into the central bore portion 92C of the hydraulic piston 56 to fix the pneumatic piston 94 in position relative to the hydraulic piston 56. In this manner the hydraulic 56 and pneumatic 94 pistons are coaxially mounted on a common shaft such that they move linearly together. In addition, it is readily apparent that by housing the ankle unit 16 and joint mechanism 18 within the housing 48, the ankle unit 12 can be made more compact. Furthermore, since the end cap 74 functions as a partition, i.e., a common wall, to both the hydraulic cylinder 54 and the pneumatic cylinder 106 this additionally contributes to a reduced overall height of the ankle unit 16.

A bulkhead cap 102 is disposed over the pneumatic piston 94. The bulkhead cap 102 has a descending skirt 104 which, along with a proximal wall 74P of the end cap 74, defines a pneumatic chamber/cylinder 106 within which the pneumatic piston 94 is adapted to oscillate. The skirt 104 does not extend all the way down to the end cap 74 but there is gap 126 between a distal edge of the skirt 104 and the proximal wall 74P of the end cap 74. A pneumatic piston quad ring 108 is disposed in an annular groove 110 around the pneumatic piston 94, to form an airtight seal between the pneumatic piston 94 and an inner wall 104A of the bulkhead cap's skirt 104. An outer wall 104B of the skirt 104 is threaded for fixing the bulkhead cap 102 into the inner surface 50 of the housing 48. An O-ring 112 is disposed between the bulkhead cap 102 and the inner surface 50 of the housing 48 to further seal the pneumatic chamber 106.

A dome 114 is disposed over the bulkhead cap 102 and mounted to the housing 48. The pyramid shin connection interface 22 is placed over the bulkhead cap 102 and a pyramid screw 116 fixes the pyramid connection interface 22 to the bulkhead cap 102.

A felt washer 118 is disposed around the distal piston rod 66. A dust cover 120 is also disposed around the distal piston rod 66 and fixed to the housing 48. A trunnion 122 is threaded into the distal bore portion 92D. A cylindrical bore 124 in the trunnion 122 receives the piston pivot 28, for pivotally connecting the hydraulic 56 and pneumatic 94 pistons to the foot component 12. As the body 48 of the ankle unit 16 pivots about the ankle flexion axis 26A, the pistons 56, 94 move substantially linearly in the housing 48.

Figure 4:
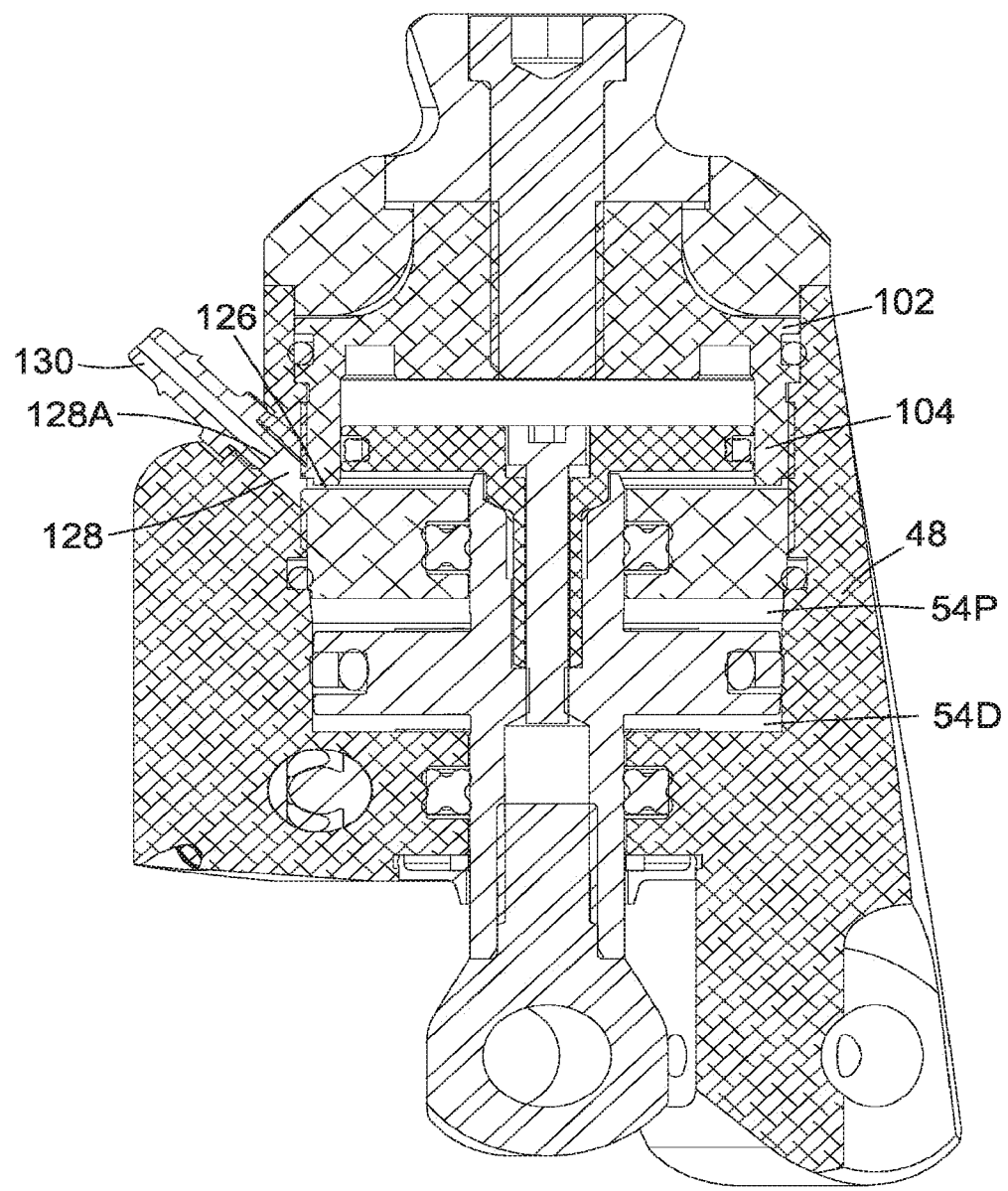
FIG. 4 is a second cross-section view of the ankle unit of FIG. 2 in the neutral position along a plane which is rotated from the anterior-posterior plane.
Figure 5:
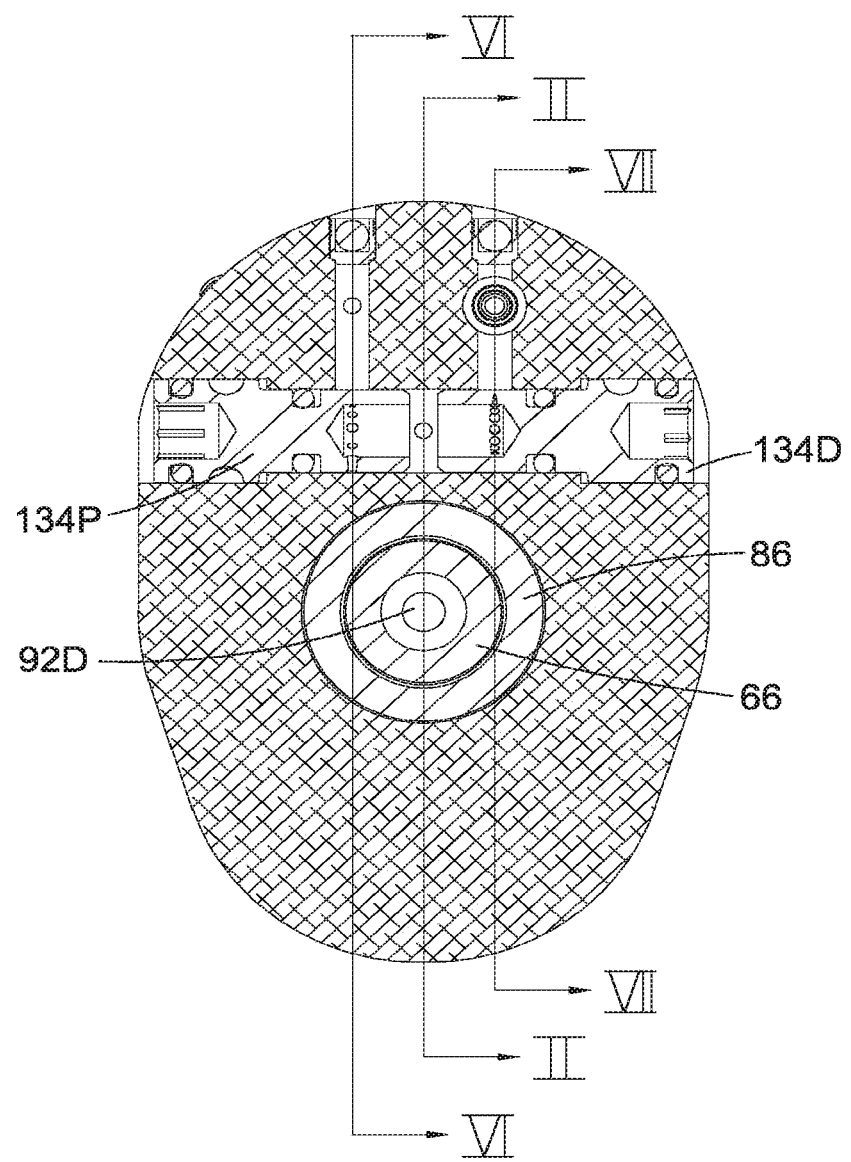
FIG. 5 is a cross-section view of the ankle unit of FIG. 2 in the direction V-V shown in FIG. 2.

FIG. 4 is a second cross-section view of the ankle unit 16 of FIG. 2 in the neutral position along a plane which is rotated from the anterior-posterior plane. In this view it can be seen that the gap 126 between the descending skirt 104 of the bulkhead cap 102 and the end cap 74 is in communication with a passage 128 in the housing 48. A barb fitting 130 is mounted to an end 128A of the passage 128 in the housing 48 to provide an inlet port/external vacuum connection which is in communication with the pneumatic cylinder 106. Tubes 40A, 40B, 40C (shown in FIG. 1) are connected to the barb fitting 130 in series at their first end and connected to the socket 36 at their second end.

The hydraulic cylinder 54 is divided into proximal 54P and distal 54D chambers. These chambers 54P, 54D are linked by two hydraulic bypass passages 132A, 132B in the ankle unit body 30, the first passage 132A being visible in FIG. 6 and the second passage 132B being visible in FIG. 7. These two bypass passages 132A, 132B communicate with the proximal chamber 54P of the hydraulic cylinder 54 via a common linking passage 136 (visible in FIG. 2) which opens into the distal chamber 54D.

The two hydraulic bypass passages 132A, 132B, each contain a damping resistance control valve 134P, 134D constituting a manually adjustable area orifice, and a non-return valve 138A, 138B.

Figure 6:
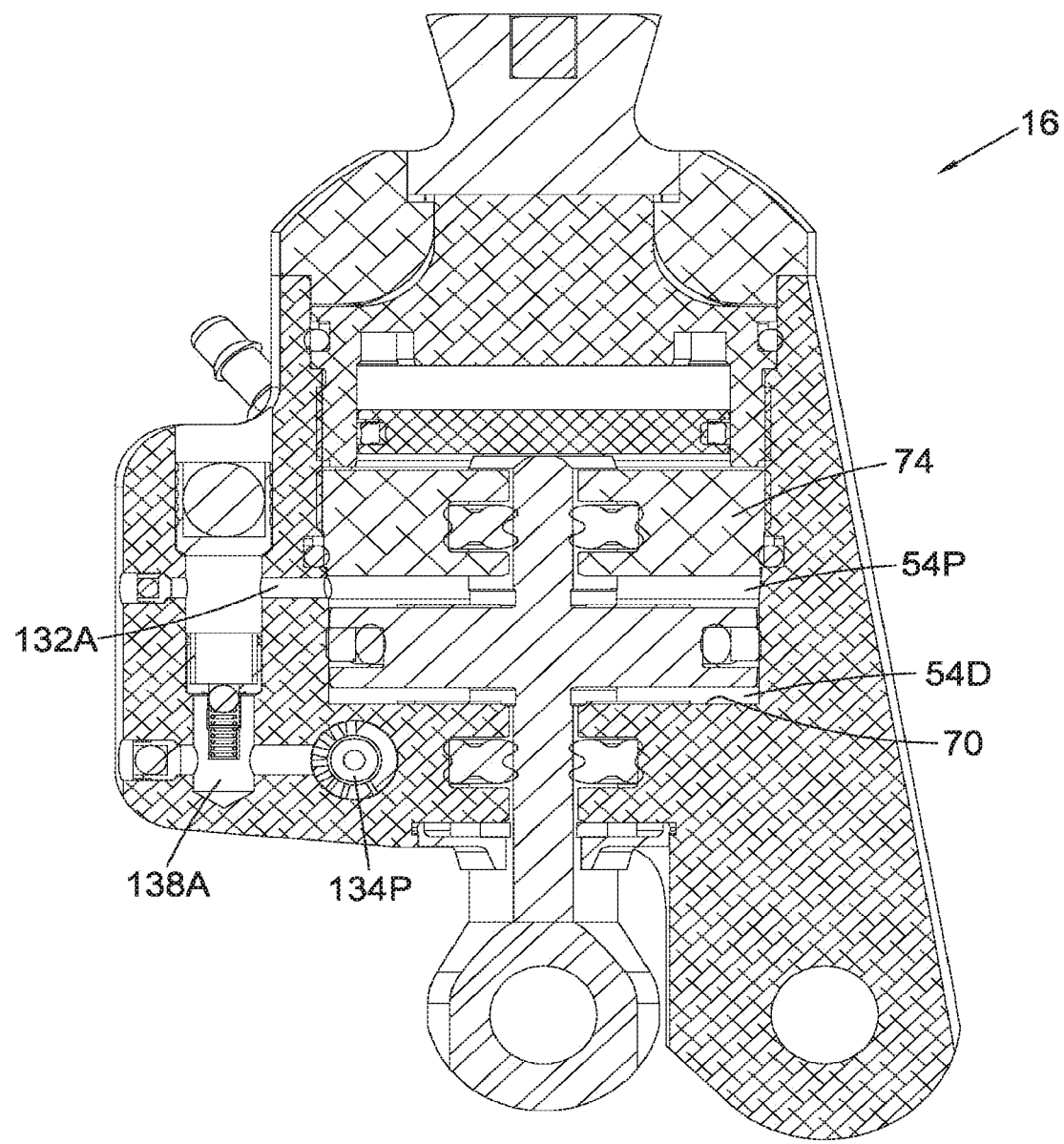
FIG. 6 is a cross-section view of the ankle unit of FIG. 2 in the direction VI-VI shown in FIG. 5.
Figure 7:
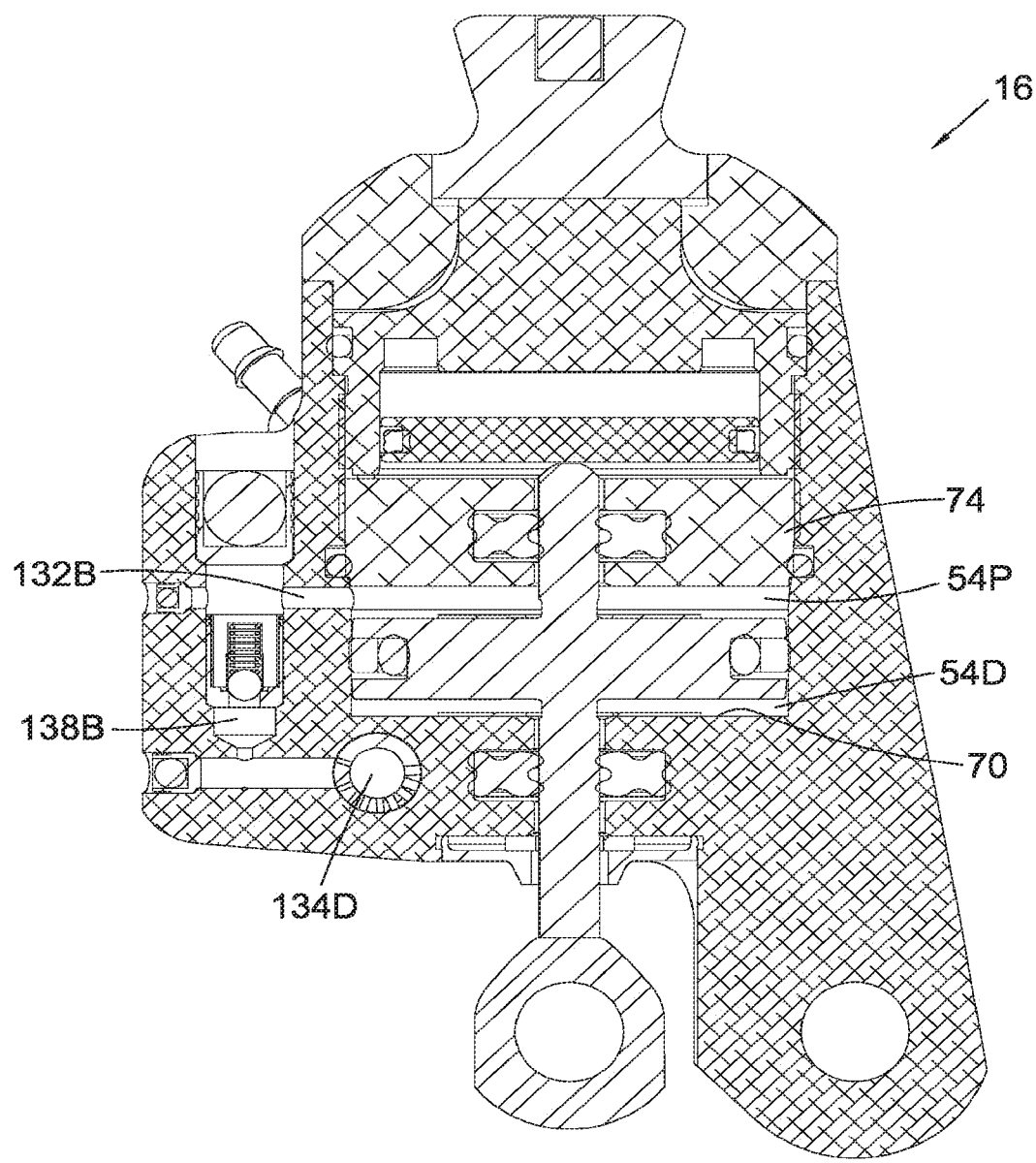
FIG. 7 is a cross-section view of the ankle unit of FIG. 2 in the direction VII-VII shown in FIG. 5.

The bypass passage 132A appearing in FIG. 6 has its non-return valve 138A oriented to allow the flow of hydraulic fluid from the proximal chamber 54P to the distal chamber 54D during plantar-flexion. The bypass passage 132B appearing in FIG. 7 has its non-return valve 138B oriented to allow the flow of hydraulic fluid from the distal chamber 54D to the proximal chamber 54P during dorsi-flexion. Continuous yielding movement of the foot component 12 relative to the ankle unit 16 about the ankle flexion axis 26A is possible between dorsi-flexion and plantar-flexion limits defined by the abutment of the joint mechanism hydraulic piston 56 with, respectively, the lower end wall 70 of the hydraulic cylinder 54 and the end cap 74. The level of damping for dorsi-flexion and plantar-flexion is independently and manually presetable by the respective adjustable-area orifices.

Typically, to mount the tubular shin component 30 to the shin connection interface 22, the shin component 30 having, at its distal end 32, an annular female pyramid receptacle having alignment screws, as well known to those skilled in the art, for adjusting the orientation of the shin component 30 relative to the ankle unit 16. At a neutral alignment position, the axis of the shin component (the shin axis) is coincident with the shin connection axis 24 (shown in FIG. 1). When the shin component 30 is affixed to the ankle unit 16 in this neutral position, the limit of dorsi-flexion of the ankle-foot prosthesis, defined by the abutment of the hydraulic piston 56 with the distal end wall 70 of the hydraulic cylinder 54 corresponds to an anterior tilt of the shin axis 24 relative to the vertical when the user stands on a horizontal surface. The plantar flexion limit, defined by abutment of the hydraulic piston 56 with the end cap 74 of the cylinder 54 corresponds to a posterior tilt of the shin axis.

In this embodiment, the anterior and posterior tilt angles of the shin connection axis 24 at the dorsi-flexion and plantar-flexion limits are 3 degrees (anterior) and 6 degrees (posterior) respectively with respect to the vertical. In other embodiments there may be other ranges of dorsi-flexion and plantar-flexion limits. For example, the dorsi-flexion limit may be 4, 5 or 6 degrees or more and the plantar-flexion limit may be 7, 8, 9 or 10 degrees or more.

The mechanical end-stops represented by the abutment of the hydraulic piston 56 with the lower 70 and upper 74 hydraulic cylinder walls define a yield range over which the ankle-foot prosthesis is free to flex during locomotion and during standing. Alteration of the shin component alignment at the shin connection interface 22 does not alter the angular magnitude of the yielding range because it is governed by the piston stroke, but it does alter the position of the limits with respect to the vertical. This also allows the prosthetist, whilst fitting the prosthesis, to adjust the alignment of the device to suit different heel height shoes without compromising the walking characteristics of the ankle.

It will be understood, therefore, that the angular range magnitude is fixed by the construction and geometry of the ankle-foot prosthesis and its hydraulic joint mechanism 18. The degrees of dorsi-flexion and plantar-flexion respectively are altered by the alignment of the shin component connection 22, as described above. It will be understood that alternative alignment interfaces can be used to adjust the positions of the dorsi-flexion and plantar-flexion limits. For instance, an anterior-posterior tilt alignment interface may be provided between the ankle unit 16 and the foot component 12.

Figure 8:
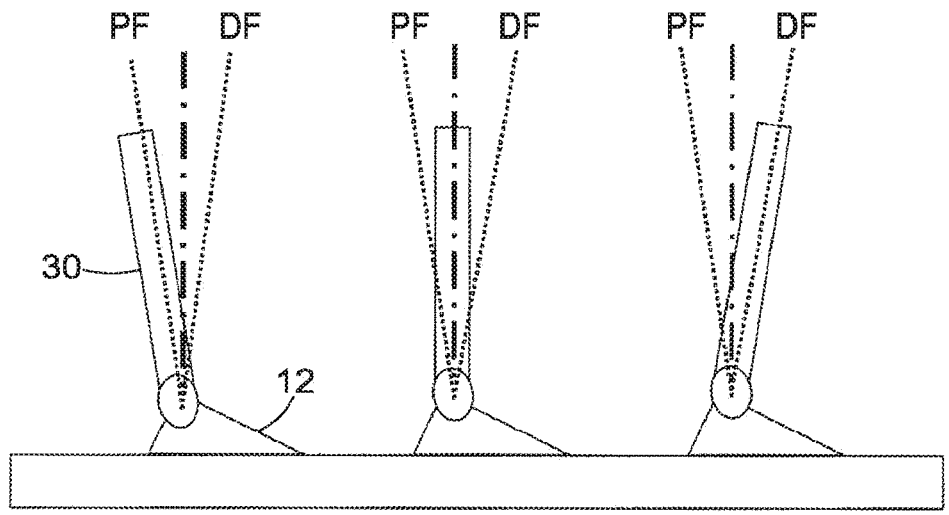
FIG. 8 is a diagram illustrating the ankle yielding range afforded by a prosthesis in accordance with the invention.

The joint mechanism allows yielding ankle flexion as shown diagrammatically in FIG. 8. The dotted lines denote plantar-flexion (PF) and dorsi-flexion (DF) limits of a mechanical hydraulic yielding range of flexion of a shin component 30 with respect to a foot component 12. The magnitude of the angular range is fixed by the geometry of the hydraulic joint mechanism 16 and its damping piston and cylinder assembly. Although in this embodiment, the range magnitude is fixed, the position of the limits with respect to a neutral position indicated by the chain lines in FIG. 8 can be altered by adjusting the alignment of the shin component 30 relative to the foot component 12 using one of the alignable connection interfaces described above. In this way, the flexion range may be biased anteriorly or posteriorly from the position shown in FIG. 8 to create a larger range of motion in either the PF or DF direction. Typical alignment settings result in a dorsi-flexion limit at 2 degrees to 6 degrees tilt anteriorly with respect to the neutral axis, dependent on the foot toe spring stiffness in particular, and the plantar flexion limit at 4 degrees to 10 degrees tilt posteriorly with respect to the neutral axis (shown by the chain lines in FIG. 8). The unit continuously allows yield in the dorsi direction (and plantar direction) up to the preset dorsi-flexion limit during walking and standing.

Providing a yielding ankle with minimal, preferably zero elastic biasing in the dorsi- or plantar directions, and with flexion limits set within the above ranges, provides advantages during stair walking and ramp walking activities, and during standing. In the normal body, the biomechanics of standing balance control are characterised by the natural balancing of external moments between joint centres of rotation. The geometrical position of the joint centres of rotations and the relative position of the body centre of gravity and the ground reaction force vector are important for stabilising action. Limb stability with a prosthetic limb during standing and walking is primarily achieved by geometrically balancing and opposing the external moments generated as the result of ground reaction force vector and in order to minimise the generation of muscle-induced internal moments. Consequently, standing can be achieved for long periods with minimal muscular effort. Walking can be achieved in an energy efficient manner. A small amount of cyclical postural sway of the upper body also helps to create stability. It follows that natural standing posture and balance control can be achieved with joints exhibiting low levels of internal resistive torque, the position of the ground reaction vector relative to the hip, knee and ankle joints being the main source of limb stability. Allowing yield in a prosthetic ankle in the manner provided by the ankle-foot prosthesis described above enables a degree of self-alignment by the user through natural proprioceptive feedback control.

Figure 9:
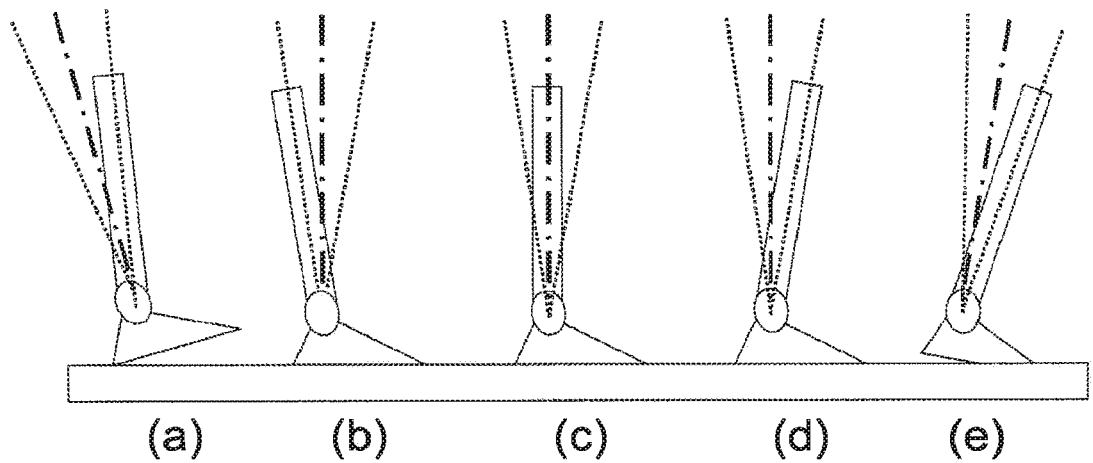
FIG. 9 is a diagram illustrating operation of a prosthesis in accordance with the invention during walking.

The dynamic action of a lower limb prosthesis having the features described above during the stance phase of walking is now described with reference to FIGS. 2, 9, 10 and 11. With reference to FIG. 9, at heel strike (a), the ankle is in a dorsi-flexed state from the roll-over actions of the previous step. In this orientation the joint mechanism 18 and vacuum mechanism 20 are in the position shown in FIG. 10. In this position the piston pivot 28 is at its lowermost point relative to the ankle flexion pivot 26 so that the hydraulic piston 56 abuts the distal nylon washer 68 which in turn is in contact with the distal end wall 70 of the hydraulic cylinder 54. In addition, the pneumatic piston 94 is at its lowest position, i.e., its closest position to the proximal wall 74P of the end cap 74. Since the pneumatic piston 94 is in near contact with the top 74P of the end cap 74 there is a minimum volume of air between the pneumatic piston 94 and the end cap 74. This feature of the invention is relevant since in a closed system with a moving piston, pressure and volume (P.V) are related such that a very low final pressure requires either a very small initial volume or a large change in volume. A large change in volume may not be practical due to the size constraints of a prosthetic device.

In an ideal scenario, the pneumatic piston 94 would be in contact with the proximal wall 74P of the end cap 74 so that when the pneumatic piston 94 is at its lowest position there is zero volume between the pneumatic piston 94 and the proximal wall 74P of the end cap 74. This would allow the piston 94 to produce the greatest vacuum in the gap 126 between the descending skirt 104 of the bulkhead cap 104, the passage 128 and within the barb fitting 130, since when the piston 94 begins to rise a pneumatic cylinder distal chamber 106D would increase in volume from a zero volume. However, in the present embodiment shown in FIG. 10 the pneumatic piston 94 is arranged to be spaced very slightly from the proximal wall 74P of the end cap 74, so that there is a non-zero volume between these parts 94, 74P. The reason for this spacing is to ensure that when the joint mechanism hydraulic piston 56 reaches its dorsi-flexion limit by abutting the distal nylon washer 68 which in turn abuts the distal end wall 70 of the hydraulic cylinder 54, the pneumatic piston 94 does not come into contact with the proximal wall 74P of the end cap 74. By preventing the pneumatic piston 94 from impacting the end cap 74, the pneumatic piston 94 can be made from a lightweight, non-structural material which reduces the overall weight of the ankle unit 16. Since the pneumatic piston 94 does not impact the end cap 74, excessive forces are not applied to the pneumatic piston 94 which makes the ankle unit 16 more reliable by eliminating the risk of failure of this part.

As the foot component 12 moves towards the flat-foot state (b), the ankle unit 16 plantar-flexes under the action of the foot heel spring 12C. As the ankle joint 16 plantar-flexes the pistons 56, 94 rise in the housing 48, passing through the position shown in FIG. 2, and causing hydraulic fluid to flow from the hydraulic cylinder proximal chamber 54P through the passage 132A to the hydraulic cylinder distal chamber 54D. At the same time, the pneumatic piston 94 moves away from the end cap 74 to create a vacuum in the distal chamber 106D of the pneumatic cylinder 106 below the pneumatic piston 94, which is in communication, via the gap 126 and passage 128, with the barb fitting 130, the tubes 40A, 40B, 40C, 40D and the evacuation port 38 of the socket 36. This creates a partial vacuum in the socket 36, drawing away air and fluid, such as sweat, which may be present between the residuum 44 and the socket 36 as the residuum 44 is pushed into the socket 36 when the amputee transfers his/her weight onto the residuum 44. As stated above, the suspension liner 46 is perforated to allow air and fluid to be drawn away from the residuum 44. The combined action of the 'pistoning' of the residuum 44 in the socket 36 and the negative pressure produced by the pneumatic piston 94 as it rises in the pneumatic chamber 106 therefore maintains a more intimate contact between the residuum 44 and the socket 36.

Figure 11:
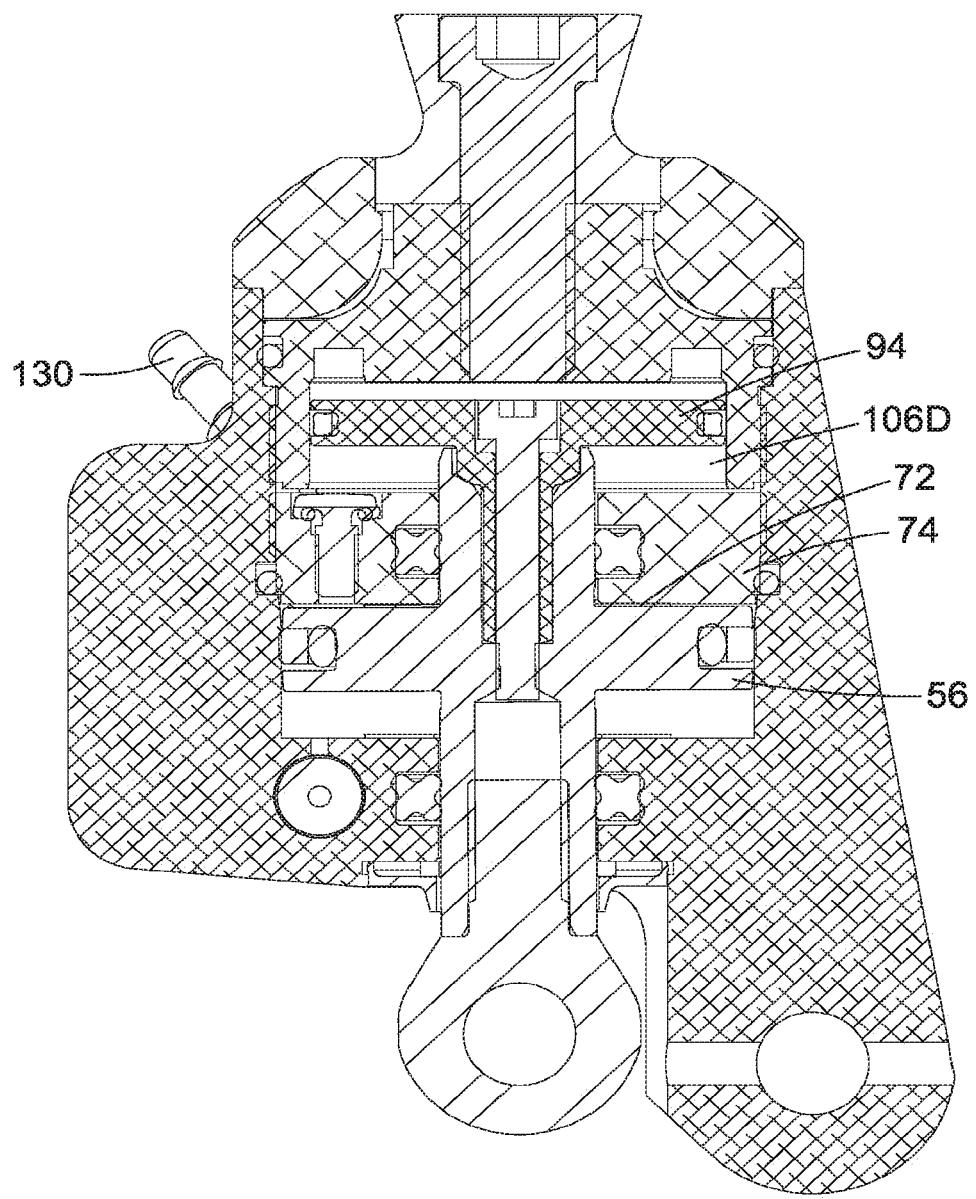
FIG. 11 is a cross-section view of the ankle unit of FIG. 2, along an anterior-posterior plane, when the ankle unit is at its plantar-flexion limit.

Plantar-flexion at the ankle unit 16 may not necessarily reach the plantar-flexion limit imposed by the ankle joint mechanism 18 of the prosthesis 10 during each gait cycle. However, on those occasions when the plantar-flexion limit is reached as shown in FIG. 11, the hydraulic piston 56 abuts the proximal nylon washer 72 which in turn abuts the end cap 74, the pneumatic piston 94 reaches its highest position within the pneumatic chamber 106, thereby maximising the volume of the pneumatic cylinder distal chamber 106D.

During roll-over (c), the ankle unit 16 begins to dorsi-flex by way of the hydraulic yield afforded by the prosthesis 10, providing a smooth roll-over action, preserving body momentum, and improving knee function and the pistons 56, 94 descend within the housing 48. As the hydraulic piston 56 moves towards the distal end wall 70 of the housing 48 hydraulic fluid is pushed from the hydraulic cylinder distal chamber 54D through the passage 132B to the hydraulic cylinder proximal chamber 54P. Simultaneously the pneumatic piston 94 moves towards the end cap 74. As the pneumatic piston 94 descends in the pneumatic cylinder 106, air or moisture which is in the pneumatic chamber 106, gap 126, passage 128 and the tubes 40B, 40C will be pushed towards the first one-way valve 42A. Since the first one-way valve 42A prevents flow of this fluid into the tube 40A the fluid will exit the tubes via the tube 40D and the second one-way valve 42B. This ankle dorsi-flexion continues during which the ankle unit 16 passes, once again, through the neutral position shown in FIG. 2.

Figure 10:
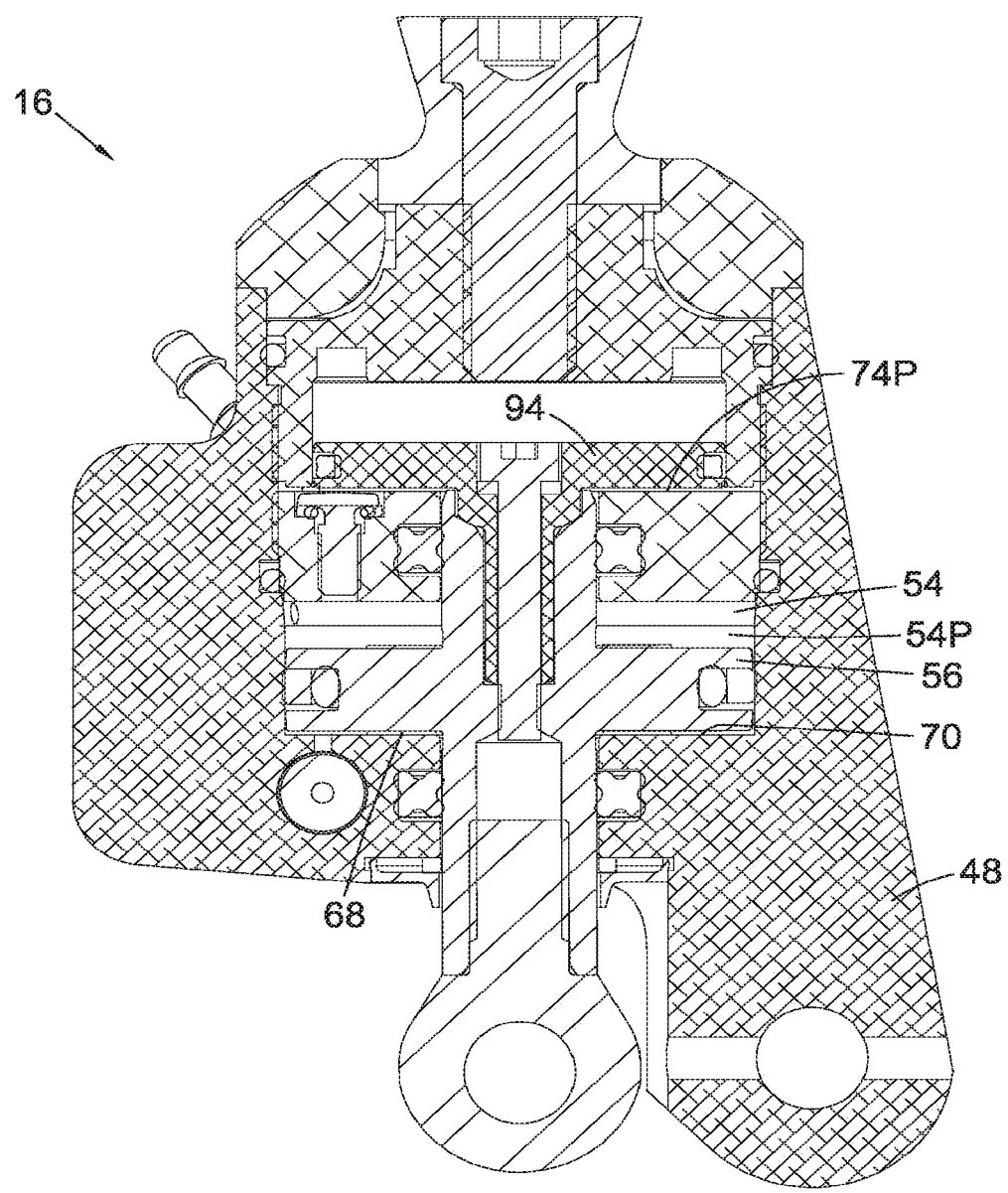
FIG. 10 is a cross-section view of the ankle unit of FIG. 2, along an anterior-posterior plane, when the ankle unit is at its dorsi-flexion limit.

Towards the end of the roll-over phase (d), the dorsi-flexion limit imposed by the joint mechanism 18 is reached and the hydraulic 56 and pneumatic 94 pistons return to their positions shown in FIG. 10. Once this happens, mechanical energy is directed into the toe spring 12B of the foot (e), to provide energy return for push-off. The swing phase is initiated with the foot 12 oriented at the dorsi-flexion end-stop 70 to provide toe clearance during the swing phase. In this position, with the pneumatic chamber 106 volume at near zero, any residual air that remains in the gap 126, passage 128, tubes 40B, 40C, 40D and joint 41 contributes to the initial volume of the pneumatic system at the start of the pneumatic piston stroke and hence determines the final pressure that can be achieved. This minimal volume of air sits in the way of fluids being removed from the socket during foot plantar-flexion and would have to be pushed ahead/expanded into the pneumatic chamber 106 first before fluids from above the one-way valve 42A can enter behind it, therefore reducing pump efficiency. This is found to alter the maximum level of vacuum that can be achieved by the system. The system, however, takes advantage of this by providing means for adjusting the vacuum created by the vacuum mechanism 20 through varying the length of the tube links 40B, 40C, 40D, which reduces the amount of 'dead' air between the first one way valve 42A and the pneumatic piston 94. Shortening one or more of these tube links 40B, 40C, 40D increases the maximum achievable vacuum level, while lengthening any of them decreases it. It is therefore obvious to those in the art that the vacuum can be further increased by eliminating any or all of the tube links 40B, 40C, 40D, for example, by placing one or both non-return valves 41A, 42B inside the ankle unit 16. The volume of air that can be expelled from the socket 36 during one cycle is limited by the diameter and stroke of the pneumatic piston 94. Consequently, it can take several steps by the amputee to generate the full vacuum pressure at the socket 36-residual limb 44 interface. This has the advantage that the vacuum is applied gently and gradually, allowing the stump to settle properly into the socket 36.

This feature of the lower limb prosthesis 10 is used in order to set up the pressure generated by the vacuum mechanism 20. During the initial set up stage by the prosthetist, a short length of tubes 40B, 40C, 40D is used between the ankle unit 16 and the first one-way valve. The amputee then takes a number of initial steps, during which the pressure gradually drops in the socket 36, until an equilibrium pressure is established in the socket 36. The amputee is then able to determine, based on sensations in the tissue of the residuum 44, if the achieved pressure is too high, in that it causes him/her discomfort. If the amputee determines that the pressure is too great then the length of the tubes 40B, 40C, 40D between the barb fitting 130 and the first one-way valve 42A is increased and the amputee once again begins to walk in order to decrease the pressure in the socket 36. This process continues until the amputee is comfortable with the pressure generated in the socket 36 based on the length of the tubes 40B, 40C, 40D.

In summary, the prosthesis 10 described above includes a foot-ankle system that is continuously allowed to yield over a limited range in plantar- and dorsi-flexion and which provides a vacuum to assist with suspension of the prosthesis 10. The yielding action is provided by a hydraulic damper joint mechanism 18 coupled to conventional foot elements (i.e. keel 12, carrier 12A and independent carbon fibre composite heel-toe springs 12B, 12C). The ankle unit 16 is, therefore, free to flex continuously over a limited plantar- and dorsi-flexion range via the hydraulic damper 18 with minimal interference from elastic elements during walking and standing. During standing, the relative positions of the hip, knee and ankle joint centres are such that substantially normal standing postures can be maintained, the moments about each joint being automatically balanced thereby creating limb stability. Moreover, the self-aligning action of the foot-ankle system facilitates improved control of energy transfer between limb segments during locomotion, the user's hip joint being the main driver and the knee joint being the main facilitator of mechanical energy transfer. This biomimetic method of stabilisation of standing stability and balance control has a further advantage in that, while standing on ramps, owing to the yielding action of the hydraulic components, there are no significant reaction moments generated around the ankle which may cause imbalance between joints and discomfort. Since, owing to the limited range of hydraulic yielding, the ankle is free to move, adaptation for walking and standing on inclined surfaces and changes to footwear with various heel heights is achieved automatically. A further advantage of the system is a smoother more progressive transition during roll-over over a variety of terrains.

The preferred construction includes an alignment adaptor to allow setting and adjustment of the plantar-flexion and dorsi-flexion hydraulic yield limits. Such adjustment allows the prosthetist to provide for balancing of limb moments during standing.

The degree of resistance to flexion in the dorsi-direction or plantar-direction is manually adjustable (e.g., by rotation of flow control valve elements 134P, 134D using a screwdriver). The control valves 134P, 134D for controlling hydraulic resistance may, in an alternative embodiment, be replaced by a single adjustable control valve in a common bypass passage, supplemented, if necessary, by a second control valve in a branch passage.

In addition, the joint provided by the ankle-foot system may be hydraulically locked at times, preferably manually, but also, for instance, remotely in real time using an electrically controlled valve, preferably operated wirelessly via a key fob. It should be noted that during those periods of time when the joint is hydraulically locked the vacuum mechanism 20 would be disabled.

The dorsi-flexion end-stop may be cushioned, e.g. by inserting a compression spring on the lower cylinder wall or on the lower face of the piston. Alternatively, a resilient elastomeric or felt pad may be provided on one of these surfaces.

In summary, the preferred foot and ankle system as described has a linear hydraulic piston arrangement for the simple control of a hydraulic damping range, and a pneumatic piston arrangement for producing a vacuum. The damping range is set mechanically, the linear piston arrangement being preferred for simplicity and reliability. Independent dorsi-flexion and plantar-flexion valve adjustment is provided, allowing improved setup and customisation of foot performance to suit the requirements of individual amputees. The preferred foot and ankle combination represents a visco-elastic structure according to the Maxwell model, i.e., the damper of the ankle joint mechanism acts in series with the resilient part of the foot. The hydraulic damping is active on a step-by-step basis, as opposed to being substantially locked on some steps.

This invention provides active suspension and works in conjunction with a perforated liner to provide enhanced suspension during the first rocker phase of walking from heel contact to foot flat. This is achieved through the natural pistoning action of the residual limb 44 into the liner 46 and socket 36 interface, which expels air and fluids due to body mass, gravitational force and walking inertia whilst simultaneously using the plantar flexion of the ankle unit 16 to generate additional vacuum. Once the ankle motion changes direction at the start of the second rocker, i.e., at the position shown in FIG. 9(*b*), and during the roll-over as shown in FIGS. 9(*c*) and 9(*d*), the additional vacuum generated is maintained via the one way valve 42A in the line 40A, 40B, 40C to the socket 36. During the third and last rocker phase of walking, i.e., from the position shown in FIG. 9(*d*) to the position shown in FIG. 9(*e*), inertia forces may be in the opposite direction to the diminishing load applied by the amputee in preparation for the swing phase of the walking cycle. At this stage the dorsi-flexion limit of the ankle joint mechanism 18 has been reached and the pneumatic piston 94 is thus primed for the next heel strike, as shown in FIG. 9(*a*). Hence this system 10 ensures close and continuous contact of the prosthesis socket 36 and liner 46 interface to the residual limb 44. This enhances suspension for proper proprioceptive feedback throughout the entire cycle of ambulation containing both stance and swing phase.

Figure 12:
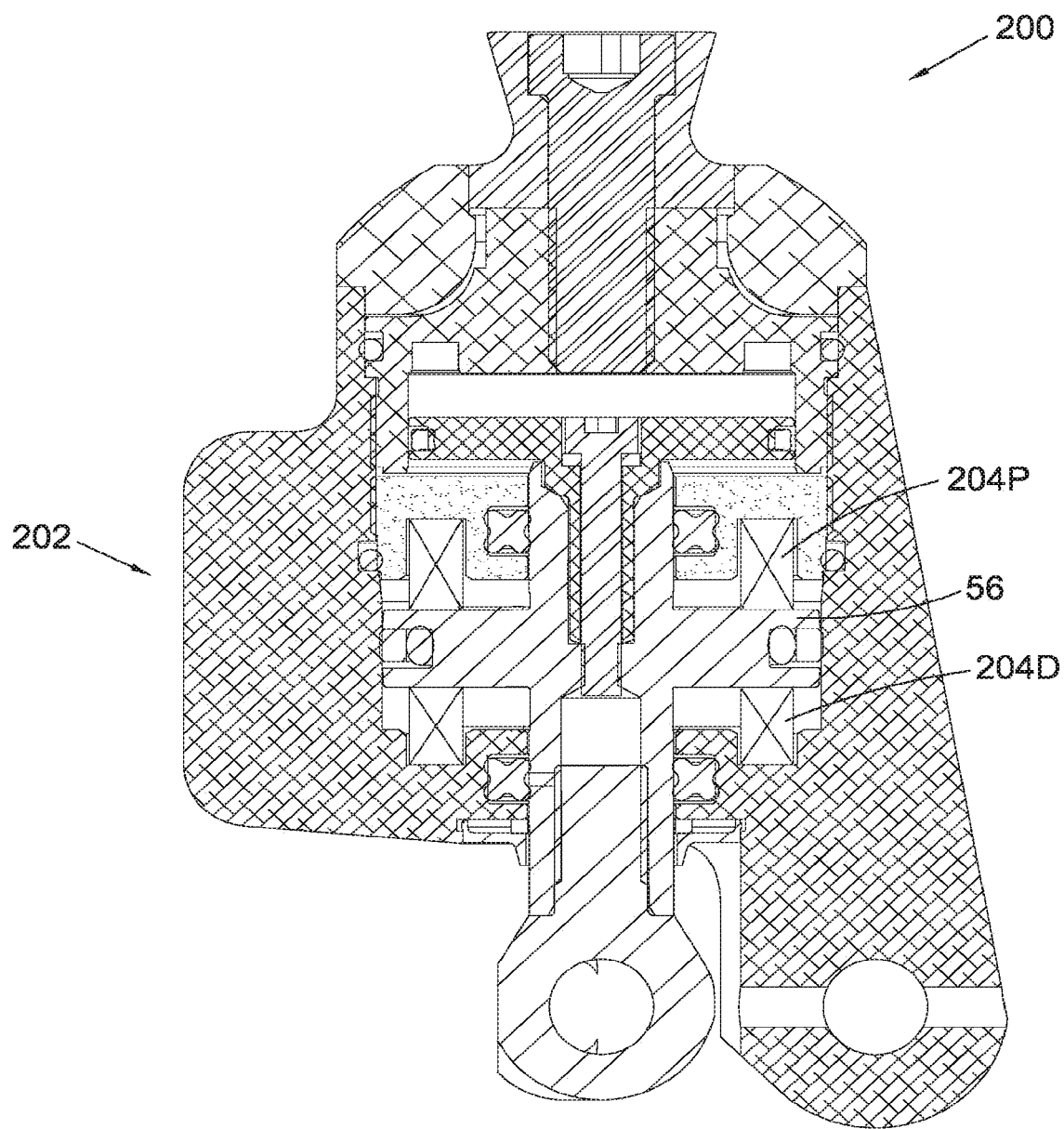
FIG. 12 is a cross-section of an ankle unit for use in a lower limb prosthesis in accordance with a second embodiment of the invention.

A further embodiment of the invention is shown in FIG. 12, which shows a non-hydraulic ankle unit 200 for producing a vacuum. The non-hydraulic ankle unit 200 is to be used with a foot component 12, shin component 30, socket 36 and suspension liner 46 as shown in FIG. 1 (by replacing the ankle unit 16 of FIG. 2) as part of a similar lower limb prosthesis system. Other than the use of a non-hydraulic joint mechanism 202 in place of the hydraulic joint mechanism 18 of FIG. 2, the skilled person will readily understand that all of the features relating to the structure and operation of the vacuum mechanism 20 are the same for the ankle unit 16 of FIG. 2 and the ankle unit 200 of FIG. 12. Note that the barb 130 of the first embodiment is not shown in FIG. 12 but is present in the non-hydraulic ankle unit 200.

Instead of the ankle unit 200 including a hydraulic joint mechanism incorporating a hydraulic piston and cylinder assembly and associated passages and valves, the ankle unit 200 includes an ankle joint mechanism 202 having two compression springs 204P, 204D, one either side of the joint mechanism piston 56. The compressions springs 204P, 204D may be made of metal or urethane. If a metal spring is used it may be a coil spring or a wave spring, such as a Smalley® Steel Ring Company CS112. If a urethane rubber spring is used then it may be any one of the urethane springs produced in multiple durometers and sizes by spring manufacturers such as Associated Spring® and Raymond®.

When the ankle joint mechanism 202 is flexed from a neutral position, the piston 56 will move linearly against a resilient biasing force of one of the compression springs 204P, 204D. Hence, whenever the ankle unit 200 is not in its neutral position the piston 56 will be subject to an urging force to return it to a neutral position where the biasing force of the compression springs is more or less equal. Removing the hydraulic mechanism from the ankle unit 200 provides a lower cost version of the ankle unit 200 than the arrangement shown in the first embodiment of the invention.

Hence, according to this embodiment the invention may provide a lower limb prosthesis comprising: a foot component; and an ankle unit pivotally mounted to the foot component, the ankle unit comprising: an ankle joint mechanism comprising a resilient piston and cylinder assembly for providing resilient damping whenever the ankle joint flexes, and a vacuum mechanism comprising a pneumatic piston and cylinder assembly for generating a vacuum, wherein the resilient and pneumatic piston and cylinder assemblies are arranged such that the vacuum mechanism generates a vacuum during plantar-flexion of the ankle unit.

Similarly, according to this embodiment there is provided a lower limb prosthesis comprising: a foot component; and an ankle unit pivotally mounted to the foot component, the ankle unit comprising a body within which is housed: an ankle joint mechanism comprising a resilient piston and cylinder assembly for providing resilient damping whenever the ankle joint flexes; and a vacuum mechanism comprising a pneumatic piston and cylinder assembly for generating a vacuum.

Various modifications will be apparent to those in the art and it is desired to include all such modifications as fall within the scope of the accompanying claims.

The ankle unit may be in the form of the ankle unit directly pivotally mounted to a prosthetic foot, as described above with reference to the Figures or it may be in the form of a two-part assembly for detachable mounting to a foot component.

In the embodiment described above the pneumatic piston is rigidly connected to the hydraulic piston so that they move in concert. In other embodiments the pneumatic piston may be connected to the hydraulic piston such that the pneumatic piston is free to move axially away from the hydraulic piston. In this manner, when the hydraulic piston rises during plantar-flexion the pneumatic piston rises at the same time. However, when the hydraulic piston falls the pneumatic piston may not necessarily fall together with the hydraulic piston and the distance between the hydraulic and pneumatic pistons may increase. In such a case, the mechanism may include a spring above the pneumatic piston to urge the pneumatic piston towards its lowest position where there is minimal volume in the pneumatic chamber between the pneumatic piston and the end cap.

In the embodiment described above, the tubes 40A, 40B, 40C, 40D, joint 41 and one-way valves 42A, 42B are mounted externally of the other components of the lower limb prosthesis 10. In other embodiments these components may be routed from the vacuum mechanism 20 of the ankle unit 16 to the socket 36 inside the hollow shin component 30. This provides the advantage that the tubes 40A, 40B, 40C, 40D are protected from snagging and also makes the lower limb prosthesis 10 tidier.

In the embodiment described above, the vacuum is generated in the socket 36 during ambulation. When the amputee wishes to remove the prosthesis 10 residual low pressure may remain in the socket 36, depending on the period which has lapsed since the amputee most recently activated the vacuum mechanism 20 during walking. Since the presence of this, at least partial, vacuum can hinder removal by the amputee of the lower limb prosthesis 10, the socket 36 may be provided with a pressure release valve in one of its walls which would allow air to enter the cavity of the socket 36, thereby equalising pressure between the inside and the outside of the socket 36.

The liner 46 referred to above is described as being porous or perforated. The liner 46 may be perforated only at its distal end, for example in the region of the evacuation port 38, it may be porous over a majority of its surface, for example excluding a region around its proximal mouth, or it may be perforated over its entire surface to allow fluids to pass from the liner-skin interface to the exterior of the entire liner. Where the perforations extend close to or beyond a proximal edge of the socket 36 it would be necessary to seal the socket edge and the liner by using a sleeve, for example as described in our granted U.S. Pat. No. 8,308,815 referred to above. Where the amputee is a below knee amputee having a short residuum below the knee joint it may be disadvantageous to have a sleeve around the proximal edge of the socket since this may impede the amputee's freedom to bend his knee. Therefore, in such cases it may be preferable to use a liner 46 which is perforated in a region which is spaced from the liner's proximal edge, to dispense with the need to use a sleeve.

The liner may not be covered with a porous wicking layer but may have a series of narrow axial grooves on its outside along which moisture or air may be drawn. Alternatively there may be channels in the internal surface of the socket. If such alternative methods for drawing moisture and air away from the liner to the evacuation port are used then it may be unnecessary to use a sealing mechanism at the proximal part of a liner, between a liner and the socket.

The invention claimed is:

1. A lower limb prosthesis comprising:
   a foot component; and
   an ankle unit pivotally mounted to the foot component, the ankle unit comprising:
   an ankle joint mechanism, the ankle joint mechanism comprising a resilient piston and cylinder assembly for providing resilient damping whenever the ankle joint flexes, and
   a vacuum mechanism comprising a pneumatic piston and cylinder assembly for generating a vacuum,
   wherein the resilient and pneumatic piston and cylinder assemblies are arranged such that the vacuum mechanism generates a vacuum during plantar-flexion of the ankle unit.

2. A lower limb prosthesis as claimed in claim 1, wherein:
   the resilient piston and cylinder assembly comprises an ankle joint mechanism piston and an ankle joint mechanism cylinder; and
   the pneumatic piston and cylinder assembly comprises a pneumatic piston and a pneumatic cylinder, and
   the ankle joint mechanism piston and the pneumatic piston are coaxially mounted.

3. A lower limb prosthesis as claimed in claim 2, wherein the ankle joint mechanism piston and the pneumatic piston are mounted on a common shaft.

4. A lower limb prosthesis as claimed in claim 2, wherein the ankle joint mechanism cylinder and the pneumatic cylinder share a common wall.

5. A lower limb prosthesis as claimed in claim 2, wherein the pneumatic cylinder comprises a pair of pneumatic chambers on each side of the pneumatic piston and the vacuum is generated in one of the pneumatic chambers when the pneumatic piston moves to expand that chamber, wherein a volume of the pneumatic chamber which generates the vacuum is at a minimum when the ankle unit is fully dorsi-flexed.

6. A lower limb prosthesis as claimed in claim 1, the ankle joint mechanism being constructed and arranged such that the resilient damping is a predominant resistance to flexion whenever the ankle joint flexes from a neutral position.

7. A lower limb prosthesis as claimed in claim 1, wherein one or both of the resilient and pneumatic piston and cylinder assemblies are linear.

8. A lower limb prosthesis as claimed in claim 2, the ankle joint mechanism cylinder comprising a pair of ankle joint mechanism chambers on each side of the ankle joint mechanism piston, the ankle joint mechanism further comprising a biasing arrangement urging the ankle joint mechanism piston to a neutral position between the chambers of the resilient piston and cylinder assembly.

9. A lower limb prosthesis as claimed in claim 8, wherein the biasing arrangement comprises first and second biasing elements for providing dorsi-flexion damping and plantar-flexion damping respectively.

10. A lower limb prosthesis as claimed in claim 8, wherein the biasing arrangement comprises:
    a first biasing element in a first ankle joint mechanism chamber, the first biasing element arranged to urge the ankle joint mechanism piston to the neutral position when the ankle joint mechanism moves against the first biasing element when the ankle joint mechanism is dorsi-flexed; and
    a second biasing element in a second ankle joint mechanism chamber, the second biasing element arranged to urge the ankle joint mechanism piston to the neutral position when the ankle joint mechanism moves against the second biasing element when the ankle joint mechanism is plantar-flexed.

11. A lower limb prosthesis as claimed in claim 9, wherein the first and second biasing elements are compression springs.

12. A lower limb prosthesis as claimed in claim 1, wherein the foot component is an energy-storing foot which is resiliently deformable to allow dorsi-flexion of at least an anterior portion of the foot relative to an ankle-mounting portion of the foot.

13. A lower limb prosthesis as claimed in claim 2, and further comprising:
    a shin component mounted at its first end to the ankle unit and defining a shin axis;
    a socket, mounted to a second end of the shin component, the socket comprising an evacuation port; and
    means for providing the generated vacuum to the evacuation port.

14. A lower limb prosthesis as claimed in claim 13, wherein the means for providing the generated vacuum to the evacuation port comprises:
    an inlet port forming part of the ankle unit and which is in communication with the pneumatic cylinder; and
    a plurality of tubes connected in series with a one-way valve and the inlet port.

15. A lower limb prosthesis as claimed in claim 13, wherein the resilient and pneumatic piston and cylinder assemblies share a central axis which is oriented such that said axis is substantially aligned with or parallel to the shin axis.

16. A lower limb prosthesis as claimed in claim 15, wherein the ankle joint mechanism defines a medial-lateral joint flexion axis, and wherein the joint flexion axis is to the anterior of the central axis of the pneumatic and resilient piston and cylinder assemblies.

17. A lower limb prosthesis as claimed in claim 13, wherein at least one of the foot component and the shin component includes a resilient section allowing resilient dorsi-flexion of at least an anterior portion of the foot component relative to the shin axis.

18. A system for suspending a lower limb prosthesis from a residuum, the system comprising:
    a lower limb prosthesis as claimed in claim 13; and
    a porous suspension liner.

19. A system as claimed in claim 18, wherein the liner includes a fabric distribution layer disposed over its outer surface.

20. A system as claimed in claim 18, wherein the liner is perforated at least in a region of the evacuation port.

21. A lower limb prosthesis comprising:
    a foot component; and
    an ankle unit comprising a body and being pivotally mounted at a distal end of the body to the foot component at a first, ankle flexion pivot and at a second, piston pivot, wherein within the body is housed:
    an ankle joint mechanism, the ankle joint mechanism comprising a resilient piston and cylinder assembly, comprising an ankle joint mechanism piston and an ankle joint mechanism cylinder, for providing resilient damping whenever the ankle joint flexes about the first, ankle flexion pivot; and
    a vacuum mechanism comprising a pneumatic piston and cylinder assembly, comprising a pneumatic piston and a pneumatic cylinder, for generating a vacuum, wherein the ankle joint mechanism piston and the pneumatic piston are coaxially mounted.

\* \* \* \* \*